US008043575B2

(12) United States Patent
McAllister et al.

(10) Patent No.: US 8,043,575 B2
(45) Date of Patent: Oct. 25, 2011

(54) REACTOR SYSTEM AND PROCESS FOR THE MANUFACTURE OF ETHYLENE OXIDE

(75) Inventors: Paul Michael McAllister, Houston, TX (US); Alouisius Nicolaas Renee Bos, Amsterdam (NL); Michael Alan Richard, Houston, TX (US); Dominicus Maria Rekers, The Hague (NL)

(73) Assignee: Shell Oil Company, Houston, TX (US)

( * ) Notice: Subject to any disclaimer, the term of this patent is extended or adjusted under 35 U.S.C. 154(b) by 1866 days.

(21) Appl. No.: 10/815,276

(22) Filed: Apr. 1, 2004

(65) Prior Publication Data

US 2005/0019235 A1    Jan. 27, 2005

Related U.S. Application Data

(63) Continuation-in-part of application No. 10/431,035, filed on May 7, 2003, now abandoned.

(51) Int. Cl.
     *B01J 8/02*          (2006.01)
     *B01J 35/02*       (2006.01)

(52) U.S. Cl. ........................................................ 422/211
(58) Field of Classification Search .................. 422/211
See application file for complete search history.

(56) References Cited

U.S. PATENT DOCUMENTS

| | | | |
|---|---|---|---|
| 2,238,474 A | 4/1941 | McNamee et al. | 260/348 |
| 2,424,083 A | 7/1947 | Finch et al. | 252/204 |
| 2,901,441 A | 8/1959 | Waterman | 252/463 |
| 3,563,913 A | 2/1971 | de Krijger et al. | 252/463 |
| 3,563,914 A | 2/1971 | Wattimena | 252/463 |
| 3,844,981 A | 10/1974 | Cusumano | 252/471 |
| 3,895,093 A | 7/1975 | Weidenbach et al. | 423/213.5 |
| 3,937,476 A | 2/1976 | Sakai | 274/39 A |
| 3,962,136 A | 6/1976 | Nielsen et al. | 252/454 |
| 3,962,285 A | 6/1976 | Cusumano | 260/348.5 R |
| 3,972,829 A | 8/1976 | Michalko | 252/430 |
| 3,997,476 A | 12/1976 | Cull | 252/463 |
| 4,005,049 A | 1/1977 | Fields | 252/467 |
| 4,033,903 A | 7/1977 | Maxwell | 252/476 |
| 4,125,480 A | 11/1978 | Maxwell | 252/414 |
| 4,186,106 A | 1/1980 | Rebsdat et al. | 252/414 |
| 4,207,210 A | 6/1980 | Kilty | 252/463 |
| 4,212,772 A | 7/1980 | Mross et al. | 252/476 |
| 4,235,798 A | 11/1980 | Bartley et al. | 260/449 |
| 4,244,889 A | 1/1981 | Bartley et al. | 564/132 |
| 4,356,312 A | 10/1982 | Nielsen et al. | 549/534 |
| 4,358,623 A * | 11/1982 | Murphy et al. | 568/473 |
| 4,361,500 A | 11/1982 | Mathe et al. | 252/430 |
| 4,361,503 A | 11/1982 | Dwyer et al. | 252/455 |
| 4,361,504 A | 11/1982 | Solomon et al. | 252/463 |
| 4,366,092 A | 12/1982 | Winterton | 252/476 |
| 4,366,093 A | 12/1982 | Shiozaki et al. | 252/477 |
| 4,367,167 A | 1/1983 | Lee et al. | 252/472 |
| 4,368,144 A | 1/1983 | Mitsuhata et al. | 252/463 |
| 4,379,134 A | 4/1983 | Weber et al. | 423/626 |
| 4,382,149 A | 5/1983 | Krueger | 568/473 |
| 4,420,420 A | 12/1983 | Mita et al. | 502/261 |
| 4,458,032 A | 7/1984 | Rebsdat et al. | 502/348 |
| 4,471,071 A | 9/1984 | Rebsdat et al. | 502/347 |
| 4,511,671 A * | 4/1985 | Saito et al. | 502/242 |
| 4,532,231 A | 7/1985 | Johnson | 502/347 |
| 4,628,129 A | 12/1986 | Bartley | 568/864 |
| 4,645,754 A * | 2/1987 | Tamura et al. | 502/152 |
| 4,656,157 A | 4/1987 | Hofmann et al. | 502/439 |
| 4,665,048 A | 5/1987 | Van Leeuwen et al. | 502/221 |
| 4,728,634 A | 3/1988 | Boxhoorn et al. | 502/243 |
| 4,731,350 A | 3/1988 | Boxhoorn et al. | 502/231 |
| 4,761,394 A | 8/1988 | Lauritzen | 502/348 |
| 4,766,105 A | 8/1988 | Lauritzen | 502/216 |
| 4,797,270 A | 1/1989 | Cendan et al. | 423/625 |
| 4,797,279 A | 1/1989 | Karamata et al. | 424/93 |
| 4,808,738 A | 2/1989 | Lauritzen | 549/536 |
| 4,810,689 A | 3/1989 | Hayden | 502/347 |
| 4,820,675 A | 4/1989 | Lauritzen | 502/216 |
| 4,829,044 A | 5/1989 | Boxhoorn et al. | 502/348 |
| 4,837,194 A | 6/1989 | Hayden | 502/348 |
| 4,845,296 A | 7/1989 | Ahmed et al. | 564/477 |
| 4,874,739 A | 10/1989 | Boxhoorn | 502/218 |
| 4,886,917 A | 12/1989 | Knopf et al. | 568/623 |
| 4,908,343 A | 3/1990 | Bhasin | 502/218 |
| 4,916,243 A | 4/1990 | Bhasin et al. | 549/534 |
| 4,921,681 A | 5/1990 | Ozero et al. | 422/197 |
| 4,939,114 A | 7/1990 | Nojiri et al. | 502/348 |
| 4,994,587 A | 2/1991 | Notermann et al. | 549/534 |
| 4,994,588 A | 2/1991 | Kapicak et al. | 549/534 |
| 4,994,589 A | 2/1991 | Notermann | 549/534 |
| 5,037,794 A | 8/1991 | Magistro | 502/355 |

(Continued)

FOREIGN PATENT DOCUMENTS

DE              1920976        11/1969

(Continued)

OTHER PUBLICATIONS

B.E.T. (Brunauer, Emmett and Teller) Journal of American Chemical Society 60 (1938) pp. 309-316.

(Continued)

*Primary Examiner* — Glenn Caldarola
*Assistant Examiner* — Randy Boyer (57) ABSTRACT

A reactor system for the oxidation of ethylene to ethylene oxide. The reactor system includes a reactor tube that contains a packed bed of shaped support material that can include a catalytic component. The shaped support material has a hollow cylinder geometric configuration. The reactor system has specific combinations of reactor tube and catalyst system geometries.

29 Claims, 5 Drawing Sheets

U.S. PATENT DOCUMENTS

| | | | | |
|---|---|---|---|---|
| 5,055,442 | A | 10/1991 | Osaka et al. | 502/439 |
| 5,057,481 | A | 10/1991 | Bhasin | 502/208 |
| 5,100,859 | A | 3/1992 | Gerdes et al. | 502/439 |
| 5,112,795 | A | 5/1992 | Minahan et al. | 502/324 |
| 5,145,824 | A | 9/1992 | Buffum et al. | 502/216 |
| 5,187,140 | A | 2/1993 | Thorsteinson et al. | 502/348 |
| 5,254,786 | A | 10/1993 | Lin et al. | 585/645 |
| 5,364,826 | A | 11/1994 | Kemp | 502/315 |
| 5,374,748 | A | 12/1994 | Rizkalla | 549/534 |
| 5,380,697 | A | 1/1995 | Matusz et al. | 502/348 |
| 5,380,885 | A | 1/1995 | Kemp | 549/536 |
| 5,387,751 | A | 2/1995 | Hayden et al. | 549/534 |
| 5,407,888 | A | 4/1995 | Herzog et al. | 502/317 |
| 5,418,202 | A | 5/1995 | Evans et al. | 502/348 |
| 5,447,897 | A | 9/1995 | Kemp | 502/303 |
| 5,457,897 | A | 10/1995 | Becker | 34/472 |
| 5,486,628 | A | 1/1996 | Kemp | 549/536 |
| 5,502,020 | A | 3/1996 | Iwakura et al. | 502/317 |
| 5,545,603 | A | 8/1996 | Kemp | 502/347 |
| 5,588,986 | A | 12/1996 | Davis et al. | 95/211 |
| 5,597,773 | A | 1/1997 | Evans et al. | 502/348 |
| 5,626,455 | A | 5/1997 | Keller et al. | 414/288 |
| 5,663,385 | A | 9/1997 | Kemp | 549/536 |
| 5,668,077 | A | 9/1997 | Klopries et al. | 502/347 |
| 5,703,253 | A | 12/1997 | Evans et al. | 549/536 |
| 5,705,661 | A | 1/1998 | Iwakura et al. | 549/536 |
| 5,734,068 | A | 3/1998 | Klopries et al. | 549/536 |
| 5,739,075 | A | 4/1998 | Matusz | 502/302 |
| 5,801,259 | A | 9/1998 | Kowaleski | 549/536 |
| 5,935,894 | A | 8/1999 | Kanazirev | 502/341 |
| 6,103,916 | A | 8/2000 | Takada et al. | 549/534 |
| 6,281,160 | B1 | 8/2001 | Basset et al. | 502/332 |
| 6,325,919 | B1 | 12/2001 | Koyama et al. | 208/134 |
| 6,368,998 | B1 | 4/2002 | Lockemeyer | 502/347 |
| 6,372,925 | B1 | 4/2002 | Evans et al. | 549/536 |
| 6,498,122 | B2 | 12/2002 | Nakashiro | 502/347 |
| 6,511,938 | B1 | 1/2003 | Liu et al. | 502/347 |
| 6,631,890 | B1 | 10/2003 | Lau | 261/94 |
| 6,656,874 | B2 | 12/2003 | Lockemeyer | 502/347 |
| 6,717,001 | B2 | 4/2004 | Evans et al. | 549/536 |
| 7,259,129 | B2 | 8/2007 | Matusz et al. | 502/347 |
| 2002/0010094 | A1 | 1/2002 | Lockemeyer | 502/439 |
| 2002/0010378 | A1 | 1/2002 | Kakimoto et al. | 568/867 |
| 2004/0137957 | A1 | 7/2004 | Jeong | 455/566 |
| 2004/0224841 | A1 | 11/2004 | Matusz et al. | 502/347 |
| 2004/0225138 | A1 | 11/2004 | McAllister et al. | 549/523 |
| 2004/0260103 | A1 | 12/2004 | Matusz et al. | 549/534 |
| 2006/0065064 | A1 | 3/2006 | Richard et al. | 73/865.5 |
| 2008/0015393 | A1 | 1/2008 | Matusz et al. | 568/497 |

FOREIGN PATENT DOCUMENTS

| | | |
|---|---|---|
| EP | 211521 | 2/1987 |
| EP | 0266015 A1 | 10/1987 |
| EP | 327356 | 8/1989 |
| EP | 563414 | 10/1993 |
| EP | 568978 | 11/1993 |
| EP | 716884 | 6/1996 |
| EP | 0937498 | 8/1999 |
| EP | 1002575 | 5/2000 |
| EP | 1201301 | 5/2002 |
| EP | 1277698 | 1/2003 |
| FR | 2005978 | 10/1969 |
| GB | 1257352 | 4/1969 |
| GB | 1489335 | 10/1977 |
| JP | 56105750 | 8/1981 |
| JP | 56164013 | 12/1981 |
| WO | WO9623585 | 8/1996 |
| WO | WO9641848 | 12/1996 |
| WO | WO01/96324 | 12/2001 |
| WO | WO0226370 | 4/2002 |
| WO | WO03072246 | 9/2003 |
| WO | WO2004094055 | 11/2004 |
| WO | WO2004101144 | 11/2004 |
| WO | WO2005023417 | 3/2005 |

OTHER PUBLICATIONS

"Kirk-Othmer Encyclopedia of Chemical Technology". 3$^{rd}$ edition. vol. 9. 1980. pp. 432-447.

Fulton, J. W., "Selecting the Catalyst Configuration", Chemical Engineering. May 12, 1986, pp. 97-101.

W. J. Beek, K.M.K. Multzall: "Transport Phenomena", 1975, J. Wiley & Sons, XP009060252, pp. 98-120.

R. B. Bird, W. E. Stewart, and E. N. Lightfoot: "Transport Phenomena", 1960 J. Wiley & Sons, pp. 198-201.

* cited by examiner

REACTOR SYSTEM AND PROCESS FOR THE MANUFACTURE OF ETHYLENE OXIDE

This application is a continuation-in-part of U.S. patent application Ser. No. 10/431,035 filed May 7, 2003 now abandoned, the entire disclosure of which is hereby incorporated by reference.

The invention relates to reactor systems. Another aspect of the invention relates to the use of reactor systems in the manufacture of ethylene oxide.

Ethylene oxide is an important industrial chemical used as a feedstock for making such chemicals as ethylene glycol, ethylene glycol ethers, alkanol amines and detergents. One method for manufacturing ethylene oxide is by the catalyzed partial oxidation of ethylene with oxygen. In this method, a feedstream containing ethylene and oxygen is passed over a bed of catalyst contained within a reaction zone that is maintained at certain reaction conditions. Typically, the ethylene oxidation reactor is in the form of a plurality of parallel elongated tubes that are filled with supported catalyst particles to form a packed bed contained within the reactor tubes. The supports may be of any shape, such as, for example, spheres, pellets, rings and tablets. One particularly desirable support shape is a hollow cylinder.

One problem encountered with the use of a packed bed of hollow cylinder supported catalyst particles in an ethylene oxidation reaction zone is the difficulty in having a proper balance between the pressure drop that occurs across the catalyst bed during the operation of the ethylene oxide process and the catalyst bed packing density. Catalyst performance is generally improved with increased catalyst packing density in the ethylene oxidation reaction tubes; however, undesirable increases in pressure drop across the reactor generally accompany an increased catalyst packing density.

It is desirable in the manufacture of ethylene oxide by the partial oxidation of ethylene to utilize a reactor system with a packed catalyst bed having a high packing density but with minimized pressure drop across the packed catalyst bed.

It is, thus, an object of this invention to provide a reactor system suitable for use in the catalytic partial oxidation of ethylene oxide, which has a packed catalyst bed having a high packing density but still provides for a suitably low pressure drop during its operation.

Other aspects, objects, and the several advantages of the invention will become more apparent in light of the following disclosure.

In one aspect, the invention may be defined as providing a reactor system. The reactor system comprises a reactor tube that contains a shaped support material. The reactor tube has a length and diameter that define a reaction zone. Within the reaction zone is the shaped support material having a hollow cylinder geometric configuration. The hollow cylinder geometric configuration is defined by an inside diameter, an outside diameter and a length. A preferred embodiment of the reactor system includes the shaped support material having incorporated therein a catalytic component to thereby provide a supported catalyst system.

In one embodiment, the inside diameter, outside diameter and length are defined as follows. The ratio of the length to the outside diameter is in the range of from about 0.5 to about 2. When the tube diameter is less than 28 mm, the ratio of the outside diameter to the inside diameter exceeds about 2.3, and the ratio of the tube diameter to the outside diameter is in the range of from about 1.5 to about 7. When the tube diameter is at least 28 mm, the ratio of the outside diameter to the inside diameter exceeds about 2.7, and the ratio of the tube diameter to the outside diameter is in the range of from about 2 to about 10.

In another embodiment, the inside diameter, outside diameter and length are defined as follows. The ratio of the length to the outside diameter is in the range of from about 0.5 to about 2. The ratio of the outside diameter to the inside diameter provides a positive test result, as defined hereinafter. The ratio of the tube diameter to the outside diameter is in the range of from about 1.5 to about 7, when the tube diameter is less than 28 mm, and in the range of from about 2 to about 10, when the tube diameter is at least 28 mm.

Herein, "positive test result" is defined by a decrease of the quotient of a numerical value of the pressure drop per unit length of the packed bed and a numerical value of the packing density, relative to a comparison quotient of numerical values. The numerical values are obtained by testing the packed bed in a turbulent flow of nitrogen gas at a pressure of 1.136 MPa (150 psig). The comparison quotient of numerical values is obtained in an identical manner, except that the hollow cylinder geometric configuration of the same support material is defined by a nominal outside diameter of 6 mm and a nominal inside diameter of 2.6 mm, when the tube diameter is less than 28 mm, and a nominal outside diameter of 8 mm and a nominal inside diameter of 3.2 mm, when the tube diameter is at least 28 mm, and further by a ratio of the nominal length to the nominal outside diameter of 1.

According to another aspect of the invention, a process for manufacturing ethylene oxide includes introducing into a reactor system according to this invention a feedstock comprising ethylene and oxygen and withdrawing from the reactor system a reaction product comprising ethylene oxide and unconverted ethylene, if any, wherein within the reaction zone is the supported catalyst system that comprises a catalytic component supported on the shaped support material having a hollow cylinder geometric configuration.

Further, the invention provides a method of using ethylene oxide for making ethylene glycol, an ethylene glycol ether or an 1,2-alkanolamine comprising converting ethylene oxide into ethylene glycol, the ethylene glycol ether, or the 1,2-alkanolamine, wherein the ethylene oxide has been obtained by the process for preparing ethylene oxide according to this invention.

As used herein, in the context of the hollow cylinder geometric configuration the terms "inside diameter" and "bore diameter" have the same meaning and have been used herein interchangeably. Also, as used herein, the terms "carrier" and "support" have the same meaning and have been used herein interchangeably.

One method of manufacturing ethylene oxide is by the catalyzed partial oxidation of ethylene with oxygen. The process is described in general in Kirk-Othmer, Encyclopedia of Chemical Technology, Volume 9, pages 432 to 471, John Wiley, London/New York 1980. Conventional ethylene oxidation reactor systems are suitable for use in the present invention, and they include a plurality of parallel elongated tubes that have inside diameters in the range of from about 20 mm to about 60 mm and lengths in the range of from about 3 m to about 15 m. Larger tubes for use in ethylene oxidation reactor system may also be possible. The tubes are typically suitable for use in a shell-and-tube type heat exchangers and are formed into a bundle for placement into the shell of the heat exchanger. The tubes are packed with any suitable ethylene oxidation catalyst that provides for the partial oxidation of ethylene with oxygen to ethylene oxide. The shell side of the heat exchanger provides for the passage of a heat transfer medium for the removal of the heat of reaction resulting from the oxidation of ethylene and for the control of the reaction temperature within the tubes containing the ethylene oxidation catalyst.

A feedstream comprising ethylene and oxygen is introduced into the tubes of the reactor system wherein the feedstream is contacted with the ethylene oxidation catalyst, typically at temperature in the range of from about 50° C. to about 400° C., and typically under a pressure in the range of from about 0.15 MPa to about 3 MPa.

The catalyst system used in the typical ethylene oxide manufacturing processes described above are supported catalyst systems that include a support or carrier material upon which is deposited or into which is impregnated a catalytic component and, if desired, a catalyst promoter component or components.

The inventive reactor system can be used in the oxidation of ethylene to ethylene oxide and includes a combination of a reactor tube and a shaped support material that is preferably a catalyst system. The unique geometry of this combination provides various unexpected process benefits.

The catalyst system component of the inventive reactor system can include a shaped support material that supports a catalytic component. Optionally, the shaped support material also supports one or more catalyst promoter components or catalyst copromoter components. The preferred catalytic component is silver. As for the promoter component, it can include, for example, rare earth metals, magnesium, rhenium, and alkali metals, such as lithium, sodium, potassium, rubidium and cesium. Among these, rhenium and the alkali metals, in particular, the higher alkali metals, such as lithium, potassium, rubidium and cesium, are preferred. Most preferred among the higher alkali metals is cesium. Either the rhenium promoter may be used without an alkali metal promoter being present or an alkali metal promoter may be used without a rhenium promoter being present or a rhenium promoter and an alkali metal promoter can both be present in the catalyst system. In addition to the aforementioned promoters, a rhenium copromoter can be present in the catalyst system. Such copromoters can include sulfur, molybdenum, tungsten, and chromium. The promoter and copromoter compounds can be applied to the support material by any suitable method, for example by impregnation, and in any form.

The support material of the shaped support material and of the catalyst system can be any commercially available heat-resistant and porous material suitable for use as support material for the silver catalyst and promoter components of the catalyst system. The support materials should be relatively inert under the reaction conditions prevailing in the oxidation of ethylene, and in the presence of the chemical compounds used. The support material can include carbon, carborundum, silicon carbide, silicon dioxide, aluminum oxide and mixtures based on aluminum oxide and silicon dioxide. α-alumina is preferred, since it has a largely uniform pore diameter. The support material has typically a specific surface area of 0.1 to 10 $m^2/g$, preferably 0.2 to 5 $m^2/g$ and more preferably from 0.3 to 3 $m^2/g$ (measured by the well-known B.E.T. method, see Brunauer, Emmet and Teller in *J. Am. Chem. Soc.* 60 (1938) 309-316, which is incorporated herein by reference); typically a specific pore volume of from 0.1 to 1.5 $cm^3/g$, preferably from 0.2 to 1.0 $cm^3/g$ and most preferably from 0.3 to 0.8 $cm^3/g$ (measured by the well-known water adsorption method, that is ASTM C20); typically an apparent porosity of 20 to 120% by volume, preferably 40 to 80% by volume (measured by the water adsorption method); typically a mean pore diameter of 0.3 to 15 μm, preferably 1 to 10 μm; and typically a percentage of pores having a diameter of 0.03 to 10 μm of at least 50% by weight (measured by mercury intrusion to a pressure of $3.0 \times 10^8$ Pa using a Micromeretics Autopore 9200 model (130° contact angle, mercury with a surface tension of 0.473 N/m, and correction for mercury compression applied).

The silver catalyst component and promoter components of the catalyst system are deposited on or impregnated into the support material of the catalyst system by any standard method known in the art. The catalyst system should typically have a concentration of silver or silver metal in the range of from about 2 weight percent to about 30 weight percent, or even higher, for example up to about 40 weight percent, or up to about 50 weight percent, with the weight percent being based on the total weight of the catalyst system including the weight of the support material, the weight of the catalyst component, i.e., silver metal, and the weight of the promoter component or components. In some embodiments, it is preferred for the silver component of the catalyst system to be present at a concentration in the range of from about 4 weight percent to about 22 weight percent and, most preferably, from 6 to 20 weight percent. In other embodiments, it is preferred for the silver component of the catalyst system to be present at a concentration in the range of from more than about 20 to less than about 30 weight percent and, more preferably, from 22 to 28 weight percent. The promoter or promoters can be present in the catalyst system at a concentration in the range of from about 0.003 weight percent to about 1.0 weight percent, preferably from about 0.005 to about 0.5 weight percent and, most preferably, from 0.01 to 0.2 weight percent.

The inventive reactor system provides for an improved balance of the tube packing density (TPD), also the bed voidage and the catalyst hold-up, relative to the pressure drop across the packed bed when in use in an ethylene oxide manufacturing process, as compared to conventional systems. An important aspect of this invention is the recognition that such an improvement can be obtained, for example, by changing the ratio of the nominal outside diameter to the nominal inside diameter of the hollow cylinder geometric configuration. This is truly unexpected because catalysts based on hollow cylinder support materials have been employed in processes for the manufacture of ethylene oxide already for many years and much effort has been devoted to improving the performance of such catalyst. However, attempts to improve the performance of these catalysts by modifying the geometry of the hollow cylinder geometric configuration do not seem to have received attention.

In accordance with this invention, the improved balance is obtained, for example, by changing, typically increasing, the ratio of the nominal outside diameter to the nominal inside diameter of the hollow cylinder geometric configuration, compared to the ratio of conventional hollow cylinder support material. The improved balance may be found by comparative testing, as described hereinbefore, using a hollow cylinder support material versus a standard hollow cylinder support material having the employed dimensions as conventionally employed. In this comparative testing the materials typically have the same material density. Otherwise, a difference in material densities is corrected for, so that changes in the tube packing density reflect truly changes in the catalyst hold-up and the bed voidage. A positive test result, as defined hereinbefore, is indicative of an improved balance. Examples of the comparative testing have been provided in Examples I-IV, hereinafter.

An improved balance of the tube packing density (TPD) relative to the pressure drop across the packed bed may come in various appearances or qualities, as will be apparent from the description hereinafter.

The inventive reactor system includes a packed bed of the shaped support material or catalyst system having a greater tube packing density than is found in conventional reactor systems. In many instances, it is desirable to increase the tube packing density because of the resulting benefits in catalyst performance. However, it is generally expected that to obtain higher tube packing densities, the pressure drop across the packed bed when in use will increase relative to standard reactor systems. The inventive reactor system, on the other hand, unexpectedly provides for less of an incremental increase in the pressure drop across the packed bed contained within the reactor tube of the reactor system than is expected, and, in many cases, a decrease in pressure drop across the packed bed, when compared to conventional systems, without a corresponding loss in tube packing density and, in many instances, with an increase in tube packing density.

It is preferred for the inventive reactor system to include a packed bed having a tube packing density at least as great as is found in conventional reactor systems, but preferably exceeding the tube packing densities seen in conventional systems, that when in use exhibit pressure drops that decrease with the aforementioned increase in tube packing density.

The relative geometries between the tube diameter and the shaped supports and/or catalyst systems is an important feature of the inventive reactor system, which includes the combination of a reactor tube packed with a bed of shaped supports which preferably include catalytic components to provide the catalyst systems. It is also unexpected that larger supports, relative to the reactor tube, can be loaded as a packed bed within the reactor tube to obtain an increase in tube packing density either without observing a larger pressure drop across the packed bed when the reactor system is in use or with observing an incremental increase in pressure drop that is less than expected, particularly based on certain engineering correlations, for example the Ergun Correlation, see W. J. Beek and K. M. K. Muttzall, "Transport Phenomena", J. Wiley and Sons Ltd, 1975, p. 114.

Larger supports and catalyst systems are particularly desired for use in the packed bed of the inventive reactor system with the packed bed having a greater tube packing density than is expected for the particular size of the support or catalyst system but which provides for no incremental pressure drop increase when in use and, preferably, an incremental decrease in pressure drop relative to that which is expected for reactor systems with the same tube packing density. An additional benefit can be an increase in the tube packing density.

In order to obtain the aforedescribed benefits, the inventive reactor system should include certain geometries. It has also been determined that these geometries are influenced by reactor tube diameters and, thus, the relative geometries of the reactor tube and the shaped supports are typically different for different tube diameters. For reactor tubes having an internal diameter of less than 28 mm, the ratio of the reactor tube internal diameter and support system outside diameter should be in the range of from about 1.5 to about 7, preferably, from about 2 to about 6 and, most preferably, from 2.5 to 5. For reactor tubes having an internal diameter exceeding 28 mm, the ratio of reactor tube internal diameter and catalyst support outside diameter should be in the range of from about 2 to about 10, preferably, from about 2.5 to about 7.5 and, most preferably, from 3 to 5.

The ratio of outside diameter to bore or inside diameter of the support of the catalyst system is another important feature of the inventive reactor system. For reactor tubes having an internal diameter of less than 28 mm, the ratio of outside diameter to bore or inside diameter of the support of the catalyst system can be in the range of from about 2.3 to about 1000, preferably, from about 2.6 to about 500 and, most preferably, from 2.9 to 200. For reactor tubes having an internal diameter exceeding 28 mm, the ratio of outside diameter to bore or inside diameter of the support of the catalyst system can be in the range of from about 2.7 to 1000, preferably, from about 3 to about 500 and, most preferably, from 3.3 to 250.

While it is important for the bore diameter of the shaped support material to be relatively small, it is also important for the inside bore of the support to have at least some dimension. It has been found that the void space defined by the bore diameter provides for certain benefits in the manufacturing of the catalyst and its catalytic properties. While not wanting to be bound to any particular theory, it is believed, however, that the void space provided by the bore diameter of the hollow cylinder allows for improved deposition of the catalytic component onto the carrier, for example by impregnation, and improved further handling, such as drying. An advantage of applying a relatively small bore diameter is also that the shaped support material has higher crush strength relative to a support material having a larger bore diameter. It is preferred to have at at least one end of the bore, typically at both ends, a bore diameter of at least about 0.1 mm, more preferably at least about 0.2 mm. Preferably the bore diameter is at least about 5 mm, and preferably up to about 2 mm, for example about 1 mm or about 1.5 mm.

A further important feature of the inventive reactor system is for the support of the catalyst system of the packed bed of the inventive reactor system to have a length-to-outside diameter ratio in the range of from about 0.5 to about 2.0, preferably from about 0.8 to about 1.5 and, most preferably, from 0.9 to 1.1.

A summary of the desired ranges for the geometric dimensions of the inventive reactor system is presented in Tables 1 and 2. Table 1 presents the relative geometries of the shaped supports for reactor tubes having diameters that are less than 28 mm. Table 2 presents the relative geometries of the shaped supports for reactor tubes having diameters that of at least 28 mm. The smaller reactor tubes can have tube diameters that range downwardly to about 21 mm or even smaller, for example about 20 mm. Thus, the tube diameter of the smaller reactor tubes of the inventive reactor system can be in the range of from about 20 mm or about 21 mm to less than 28 mm. The larger reactor tubes can have tube diameters that range upwardly to about 60 mm or even larger. Thus, the tube diameter of the larger reactor tubes of the inventive reactor system can be in the range of from 28 mm to 60 mm.

For tube diameters in the range of from 28 mm to about 60 mm, in particular when the tube diameter is about 39 mm, the ratio of the nominal outside diameter to the nominal inside diameter of the of the support is preferably:

at least about 4.5, when the outside diameter is in the range of from about 10.4 mm to about 11.6 mm; or greater than about 3.4, in particular at least about 3.6, when the outside diameter is in the range of from about 9.4 mm to about 10.6 mm; or at least about 2.6, in particular in the range of from about 2.6 to about 7.3, when the outside diameter is in the range of from about 8.4 mm to about 9.6 mm.

TABLE 1

Inventive Reactor System Geometries For Reactor Tubes Having Tube Diameters of Less Than 28 mm

| | Tube Diameter/ Catalyst System Outside Diameter | Catalyst System Length/Catalyst System Outside Diameter | Catalyst Outside Diameter/Bore Diameter |
|---|---|---|---|
| Broad | 1.5-7 | 0.5-2 | 2.3-1000 |
| Intermediate | 2-6 | 0.8-1.5 | 2.6-500 |
| Narrow | 2.5-5 | 0.9-1.1 | 2.9-200 |

TABLE 2

Inventive Reactor System Geometries For Reactor Tubes Having Tube Diameters of at Least 28 mm

| | Tube Diameter/ Catalyst System Outside Diameter | Catalyst System Length/ Catalyst System Outside Diameter | Catalyst Outside Diameter/ Bore Diameter |
|---|---|---|---|
| Broad | 2-10 | 0.5-2 | 2.7-1000 |
| Intermediate | 2.5-7.5 | 0.8-1.5 | 3.0-500 |
| Narrow | 3-5 | 0.9-1.1 | 3.3-250 |

The reactor tube length can be any length that effectively provides for the proper contact times within the reaction zone between the feed reactants and the catalyst system to give a desired reaction product. Generally, as noted above, the reactor tube length will exceed 3 m and, preferably, it is in the range of from about 3 m to about 15 m. The full length of the reactor tube can be packed with the catalyst system or any portion of the length of the reactor tube can be packed with the catalyst system to thereby provide a packed bed of the catalyst system having a bed depth. Thus, the bed depth can exceed 3 m and, preferably, it is in the range of from about 3 meters to about 15 meters.

In the normal practice of this invention, a major portion of the packed bed, of the inventive reactor system comprises the shaped support material having the geometries as described herein. Thus, typically, the packed bed of the reactor system will predominately, that is for at least 50 percent, comprise the catalyst system having the specifically defined geometries and, in particular, at least about 80 percent of the packed catalyst bed will comprise the specifically defined catalyst system, but, preferably, at least about 85 percent and, most preferably, at least 90 percent. When referring to the percent of the packed bed that comprises the catalyst system, it shall mean that the ratio of the total number of individual catalyst system particles having the particular dimensions described herein, to the total number of catalyst system particles contained in the packed bed, multiplied by 100. In another embodiment, when referring to the percent of the packed bed that comprises the catalyst system, it shall mean that the ratio of the bulk volume of the catalyst system particles having the particular dimensions described herein, to the bulk volume of all the catalyst system particles contained in the packed bed, multiplied by 100. In yet another embodiment, when referring to the percent of the packed bed that comprises the catalyst system, it shall mean that the ratio of the weight of the catalyst system particles having the particular dimensions described herein, to the weight of all the catalyst system particles contained in the packed bed, multiplied by 100.

The tube packing density of the catalyst system bed of the inventive reactor system can be an important feature of the invention; since, catalyst performance improvements can result from the increase in the tube packing density obtainable from using the unique geometries of the inventive reactor system. Generally, the tube packing density of the packed catalyst system bed depends upon the associated reactor tube inside diameter and on the properties, for example, density, of the particular support material used to form the shaped support.

For smaller reactor tube inside diameters the tube packing density of the packed bed can generally be less than the tube packing density of the packed bed of larger reactor tube inside diameters. Thus, for example, the tube packing density of the packed bed of an inventive reactor system having an inside reactor tube diameter of about 21 mm can be as low as, but exceeding, about 550 kg per cubic meters when the support material is predominantly α-alumina. For reactor tubes having larger inside tube diameters as well as those having smaller diameters, it is desirable to have as great a tube packing density as is achievable and still realize the benefits of the invention. Such a tube packing density when the support material is predominantly α-alumina can exceed about 650 kg per cubic meter or can be greater than about 700 kg per cubic meter and even greater than 850 kg per cubic meter. Preferably, the tube packing density is greater than about 900 kg per cubic meter and, most preferably, the tube packing density exceeds 920 kg per cubic meter. The tube packing density will generally be less than about 1200 kg per cubic meter and, more specifically, less than 1150 kg per cubic meter.

Figure 1:
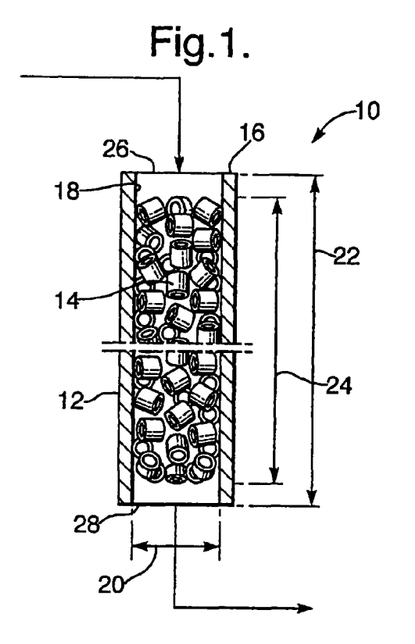
FIG. 1 depicts certain aspects of the inventive reactor system that includes a tube having a length that is packed with a packed bed comprising the shaped support material of a catalyst system.

Reference is now made to FIG. 1 which depicts the inventive reactor system 10 comprising an elongated tube 12 and a packed bed 14 contained within elongated tube 12. Elongated tube 12 has a tube wall 16 with an inside tube surface 18 and inside tube diameter 20 that define a reaction zone, wherein is contained packed bed 14, and a reaction zone diameter 20. Elongated tube 12 has a tube length 22 and the packed bed 14 contained within the reaction zone has a bed depth 24. Outside the bed depth 24, the elongated tube 12 may contain a separate bed of particles of a non-catalytic material for the purpose of, for example, heat exchange with a feedstock and/or another such separate bed for the purpose of, for example, heat exchange with a reaction product. The elongated tube 12 further has an inlet tube end 26 into which a feedstock comprising ethylene and oxygen can be introduced and an outlet tube end 28 from which a reaction product comprising ethylene oxide and ethylene can be withdrawn. It is noted that the ethylene in the reaction product, if any, is the ethylene of the feedstock which passes through the reactor zone unconverted. Typical conversions of the ethylene exceed 10 mole percent, but, in some instances, the conversion may be less.

Figure 2:
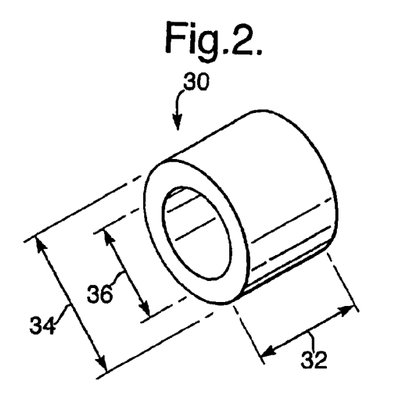
FIG. 2 depicts the shaped support material of the catalyst system of the invention and which has a hollow cylinder geometric configuration and the physical dimensions that characterize the shaped support material.

The packed bed 14 contained within the reaction zone is composed of a bed of supported catalyst system 30 as depicted in FIG. 2. The supported catalyst system 30 has a generally hollow cylinder geometric configuration with a nominal length 32, nominal outside diameter 34, and nominal inside or bore diameter 36, in accordance with this invention.

Figure 7A:
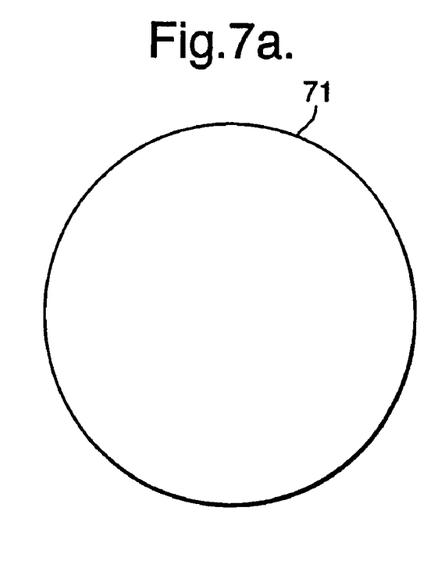
FIG. 7 depicts drawings of the cross-sections of the outside perimeters of (a) the shaped support material being an ideal cylinder, and (b) a cross-section of the shaped support material being a deviation from an ideal cylinder.
Figure 7B:
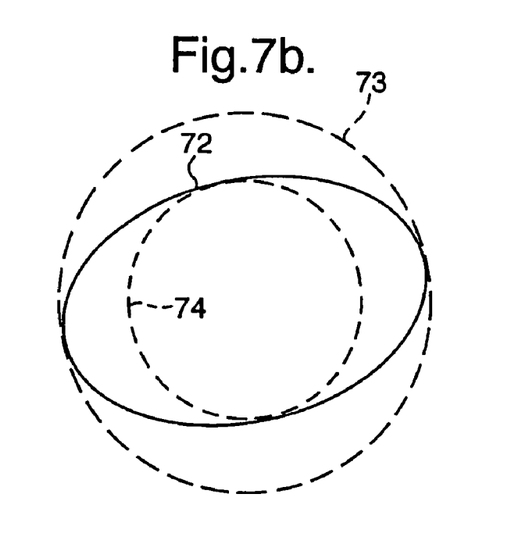

The skilled person will appreciate that the expression "cylinder" does not necessarily mean that the hollow cylinder geometric configuration comprises an exact cylinder. The expression "cylinder" is meant to include insignificant deviations from an exact cylinder. For example, the cross-section of the outer perimeter of the hollow cylinder geometric configuration perpendicular to the cylinder axis is not necessarily an exact circle 71, as depicted in FIG. 7. Also, the axis of the hollow cylinder geometric configuration may be approximately straight and/or the outside diameter of the hollow cylinder geometric configuration may be approximately constant along the axis. Insignificant deviations include, for example, cases where the outside perimeter of the cylinder can be positioned in an imaginary tube-shaped space defined by two imaginary exact coaxial cylinders of virtually the same diameters, whereby the diameter of the imaginary inner cylinder is at least 70%, more typically at least 80%, in particular at least 90%, of the diameter of the imaginary outer cylinder, and the imaginary cylinders are chosen such that the ratio of their diameters is the closest possible to 1. In such cases the diameter of the imaginary outer cylinder is deemed to be the outer diameter of the hollow cylinder geometric configuration. FIG. 7 depicts in a cross-sectional view, taken perpendicular to the axis of the imaginary cylinders 73 and 74, the outside perimeter 72 of the hollow cylinder geometric configuration, the imaginary outer cylinder 73 and the imaginary inner cylinder 74.

Similarly, the skilled person will appreciate that the bore of the hollow cylinder geometric configuration may not be necessarily exactly cylindrical, the axis of the bore may be approximately straight, the bore diameter may be approximately constant, and/or the axis of the bore may be displaced, or may angle, relative to the axis of the cylinder. If the bore diameter changes over the length of the bore, the bore diameter is deemed to be the largest diameter at a bore end. If the bore does not is not exactly circular in cross-section, the widest dimension is deemed to be the bore diameter. Also, the void space provided by the bore may be divided over two or more bores, for example 2, 3, or even 4, or 5 bores, in which case the diameters of the bores are such that the total of the cross-sectional areas of the bores is equal to the cross-sectional area of a single bore having a diameter, as specified herein.

In preferred embodiments, the hollow cylinder geometric configuration is intended to be a cylinder having a bore along the axis of the cylinder.

It is understood that the dimensions of the hollow cylinder geometric configuration are nominal and approximate, since, methods of manufacturing the shaped agglomerates are not necessarily precise.

It is the unique geometric combination of inside tube diameter or reaction zone diameter 20 and the geometric dimensions of the supported catalyst system 30 that provides for the unexpected reduction in pressure drop, when in use and relative to conventional systems, without a significant decrease in tube packing density. In many instances, and preferably, the tube packing density of the inventive reaction system is greater than that of conventional systems while still providing for a reduction in pressure drop when in use.

An essential geometric dimension of the catalyst system 30 is the ratio of nominal length 32 to nominal outside diameter 34. This dimension is described in detail above.

Another essential geometric dimension of the catalyst system 30 is the ratio of the nominal outside diameter 34 to nominal inside diameter 36. This dimension is described in detail above.

The relative dimensions between the catalyst system 30 and elongated tube 12 are an important aspect of the invention; since, these dimensions determine the tube packing density and pressure drop characteristics associated with reactor system 10. This dimension is described in detail above.

Another way of defining the catalyst system is by reference to its nominal dimensions. For a standard 8 mm catalyst having a hollow cylinder geometric configuration, the outer diameter of the cylinder is nominally 8 mm but can be in the range from about 7.4 mm to about 8.6 mm. The length of the cylinder is nominally 8 mm but can be in the range from about 7.4 mm to about 8.6 mm. For use in this invention, the bore diameter can be at least about 0.1 mm or about 0.2 mm, and preferably in the range of from about 0.5 mm to about 3.5 mm, more preferably from about 0.5 mm to less than about 3 mm.

For a standard 9 mm catalyst having a hollow cylinder geometric configuration, the outer diameter of the cylinder is normally 9 mm but can be in the range of from about 8.4 mm to about 9.6 mm. The cylinder length while nominally 9 mm can be in the range of from about 8.4 mm to about 9.6 mm. For use in this invention, the bore diameter of the standard 9 mm catalyst can be at least about 0.1 mm or about 0.2 mm, and preferably in the range of from about 0.5 mm to about 3.5 mm, more preferably from about 1.25 mm to about 3.5 mm.

For a standard 10 mm catalyst having a hollow cylinder geometric configuration, the outer diameter of the cylinder is normally 10 mm but can be in the range of from about 9.4 mm to about 10.6 mm. The cylinder length while nominally 10 mm can be in the range of from about 9.4 mm to about 10.6 mm. For use in this invention, the bore diameter of the standard 10 mm catalyst can be at least about 0.1 mm or about 0.2 mm, and preferably in the range of from about 0.5 mm to about 4.0 mm, more preferably from about 0.5 mm to about 3 mm, even more preferably from about 0.5 mm to about 2.8 mm.

For a standard 11 mm catalyst having a hollow cylinder geometric configuration the outer diameter of the cylinder is normally 11 mm but can be in the range of from about 10.4 mm to about 11.6 mm. The cylinder length while nominally 11 mm can be in the range of from about 10.4 mm to about 11.6 mm. For use in this invention, the bore diameter of the standard 11 mm catalyst can be at least about 0.1 mm or about 0.2 mm, and preferably in the range of from about 0.5 mm to about 3.5 mm, more preferably from about 0.5 mm to about 2.5 mm.

Much of the variance in the catalyst system dimensions is due to the manner by which the hollow cylinder support material is manufactured. The manufacturing methods are known in the art of catalyst support manufacture and include such standard methods as extrusion methods and pill manufacturing methods.

Figure 3:
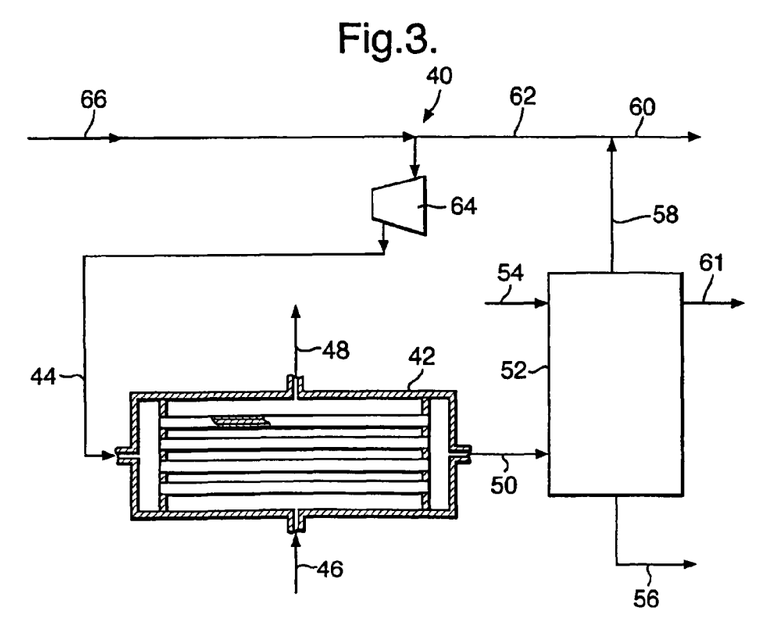
FIG. 3 is a schematic representation of an ethylene oxide manufacturing process which includes certain novel aspects of the invention.

FIG. 3 is a schematic representation showing generally an ethylene oxide manufacturing process 40 with a shell-and-tube heat exchanger 42 which is equipped with a plurality of reactor systems as depicted in FIG. 1. Typically the reactor system of FIG. 1 is grouped together with a plurality of other reactor systems into a tube bundle for insertion into the shell of a shell-and-tube heat exchanger.

A feedstock comprising ethylene and oxygen is charged via conduit 44 to the tube side of shell-and-tube heat exchanger 42 wherein it is contacted with the catalyst system contained therein. The heat of reaction is removed by use of a heat transfer fluid such as oil, kerosene or water which is charged to the shell side of shell-and-tube heat exchanger 42 by way of conduit 46 and the heat transfer fluid is removed from the shell of shell-and-tube heat exchanger 42 through conduit 48.

The reaction product comprising ethylene oxide, unreacted ethylene, unreacted oxygen and, optionally, other reaction products such as carbon dioxide and water, is withdrawn from the reactor system tubes of shell-and-tube heat exchanger 42 through conduit 50 and passes to separation system 52. Separation system 52 provides for the separation of ethylene oxide and ethylene and, if present, carbon dioxide and water. An extraction fluid such as water can be used to separate these components and is introduced to separation system 52 by way of conduit 54. The enriched extraction fluid containing ethylene oxide passes from separation system 52 through conduit 56 while unreacted ethylene and carbon dioxide, if present, passes from separation system 52 through conduit 58. Separated carbon dioxide passes from separation system 52 through conduit 61. A portion of the gas stream passing through conduit 58 can be removed as a purge stream through conduit 60. The remaining gas stream passes through conduit 62 to recycle compressor 64. A feedstream containing ethylene and oxygen passes through conduit 66 and is combined with the recycle ethylene that is passed through conduit 62 and the combined stream is passed to recycle compressor 64. Recycle compressor 64 discharges into conduit 44 whereby the discharge stream is charged to the inlet of the tube side of the shell-and-tube heat exchanger 42. Advantageously, separation system 52 is operated in such a way that the quantity of carbon dioxide in the feedstream through conduit 44 is low, for example, below 2 mole-%, preferably below 1 mole-%, or in the range of from 0.5 to 1 mole-%.

The ethylene oxide produced in the epoxidation process may be converted into ethylene glycol, an ethylene glycol ether or an alkanolamine.

The conversion into the ethylene glycol or the ethylene glycol ether may comprise, for example, reacting the ethylene oxide with water, suitably using an acidic or a basic catalyst. For example, for making predominantly the ethylene glycol and less ethylene glycol ether, the ethylene oxide may be reacted with a ten fold molar excess of water, in a liquid phase reaction in presence of an acid catalyst, e.g. 0.5-1.0% w sulfuric acid, based on the total reaction mixture, at 50-70° C. at 100 kPa absolute, or in a gas phase reaction at 130-240° C. and 2000-4000 kPa absolute, preferably in the absence of a catalyst. If the proportion of water is lowered the proportion of ethylene glycol ethers in the reaction mixture is increased. The ethylene glycol ethers thus produced may be a di-ether, tri-ether, tetra-ether or a subsequent ether. Alternative ethylene glycol ethers may be prepared by converting the ethylene oxide with an alcohol, in particular a primary alcohol, such as methanol or ethanol, by replacing at least a portion of the water by the alcohol.

The conversion into the alkanolamine may comprise reacting ethylene oxide with an amine, such as ammonia, an alkyl amine or a dialkylamine. Anhydrous or aqueous ammonia may be used. Anhydrous ammonia is typically used to favor the production of monoalkanolamine. For methods applicable in the conversion of ethylene oxide into the alkanolamine, reference may be made to, for example U.S. Pat. No. 4,845,296, which is incorporated herein by reference.

Ethylene glycol and ethylene glycol ethers may be used in a large variety of industrial applications, for example in the fields of food, beverages, tobacco, cosmetics, thermoplastic polymers, curable resin systems, detergents, heat transfer systems, etc. Alkanolamines may be used, for example, in the treating ("sweetening") of natural gas.

The following examples are intended to illustrate the advantages of the present invention and are not intended to unduly limit the scope of the invention.

EXAMPLE I

This Example I presents the testing procedure used to evaluate the pressure drop and tube packing density characteristics of the inventive reactor system relative to a standard reactor system.

Various hollow cylinder carriers having different sizes and geometries were tested in a commercial length reactor tube of either a 39 mm internal diameter or a 21 mm internal diameter. The reactor tubes were set up to measure differential pressure drop across the carrier bed. Tube packing density of the carrier bed was determined.

The particular carrier to be tested was loaded into the reactor tube using a standard funnel loading process. The carrier was weighed to determine its mass prior to being charged to the reactor tube. After the reactor tube was charged with the carrier, a 0.79 MPa (100 psig) air source was used to perform a 15 second dust blow down. The carrier bed height was measured.

The tube packing density was determined by using the mass of carrier loaded into the reactor tube, the measured height of the carrier bed, and the internal diameter of the reactor tube. The tube packing density has units of mass per volume and is defined by the following formula:

$$4m/\pi d^2 h$$

where:
  m is the mass of the carrier loaded into the reactor tube,
  d is the diameter of the reactor tube, and
  h is the height of the carrier bed contained within the reactor tube.

After the reactor tube was loaded with the carrier, it was sealed and pressure tested at 1.342 MPa (180 psig). The reactor tube was equipped with an inlet and an outlet. Nitrogen gas was introduced into the inlet of the packed reactor tube at a pressure of about 1.136 MPa (150 psig). For each of about 11 different nitrogen gas flow rates in a turbulent flow regime (Reynolds particle number in excess of about 700, see W. J. Beek and K. M. K. Muttzall, "Transport Phenomena", J. Wiley and Sons Ltd, 1975, p. 114) a differential pressure drop (pressure drop) across the carrier bed of the reactor tube was determined by measuring the tube inlet pressure and the tube outlet pressure. The inlet and outlet temperatures of the nitrogen gas were also measured. The pressure drop was evaluated per unit length of packed bed. The tube packing densities were corrected for small differences in the intrinsic material densities of the different carriers, in order to reflect differences in the catalyst hold-up caused by the differences in carrier geometries.

EXAMPLE II

Figure 4:
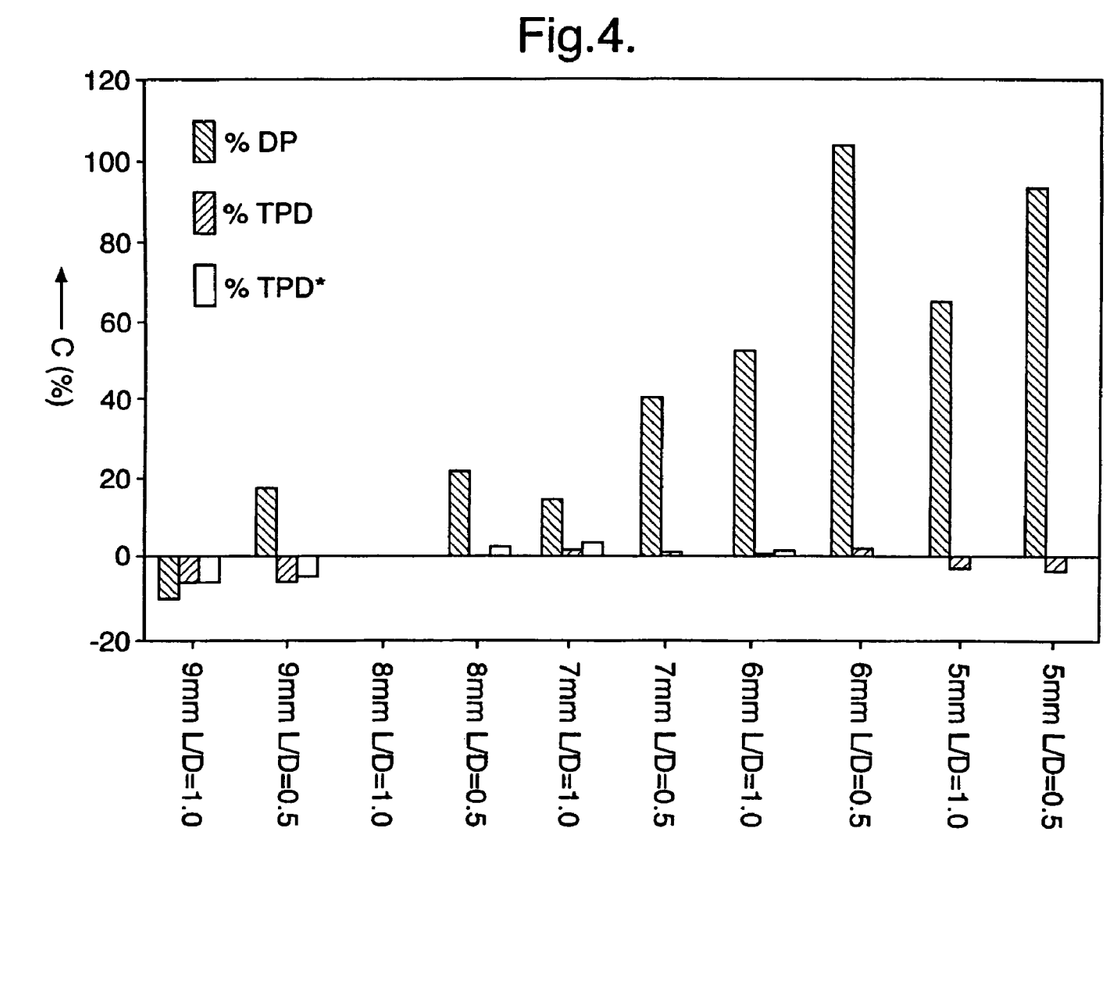
FIG. 4 presents data on the changes ("C (%)") in pressure drop ("% DP") and tube packing density ("% TPD"; "% TPD*" represents duplicate data) resulting from the use of various sizes (outer diameters) of hollow cylinder support material with different length-to-diameter ratios ("L/D") in a 39 mm diameter reactor tube relative to the use of a standard 8 mm hollow cylinder support material.

This Example II presents a summary of the results from using the testing procedure described in Example I for hollow cylinder carriers of nominal sizes 5 mm, 6 mm, 7 mm, 8 mm and 9 mm having a nominal length-to-diameter (L/D) ratio of either 0.5 or 1.0 packed into a 39 mm reactor tube. The following are the particulars of the carrier dimensions:
9 mm: L/D=1.0, bore diameter 3.85 mm
9 mm: L/D=0.5, bore diameter 3.90 mm
8 mm: L/D=1.0, bore diameter 3.20 mm ("standard 8 mm")
8 mm: L/D=0.5, bore diameter 3.30 mm
7 mm: L/D=1.0, bore diameter 2.74 mm
7 mm: L/D=0.5, bore diameter 2.75 mm
6 mm: L/D=1.0, bore diameter 2.60 mm ("standard 6 mm")
6 mm: L/D=0.5, bore diameter 2.60 mm
5 mm: L/D=1.0, bore diameter 2.40 mm
5 mm: L/D=0.5, bore diameter 2.70 mm Summary data for the percent changes in pressure drop across the carrier bed and the percent changes in tube packing density relative to the standard 8 mm carrier are presented in FIG. 4. As is shown, for carrier sizes smaller than 8 mm and for all carrier sizes having an L/D ratio of 0.5, the pressure drop across the carrier bed increases. The data presented in FIG. 4 does show, however, that in a 39 mm reactor tube, the larger 9 mm carrier that has an L/D ratio of 1.0 provides an improved pressure drop relative to the standard 8 mm carrier.

EXAMPLE III

This Example III presents the results from using the testing procedure described in Example I for cylinder carriers of nominal sizes 9 mm, 10 mm, and 11 mm with a nominal L/D ratio of 1.0 into a 39 mm reactor tube. Some of the carriers were solid cylinders, other carriers were hollow cylinders with different bore diameters, as specified in FIG. 5. Summary data for the percent changes in pressure drop across the carrier bed and the percent changes in tube packing density relative to the standard 8 mm carrier are presented in FIG. 5.

Figure 5:
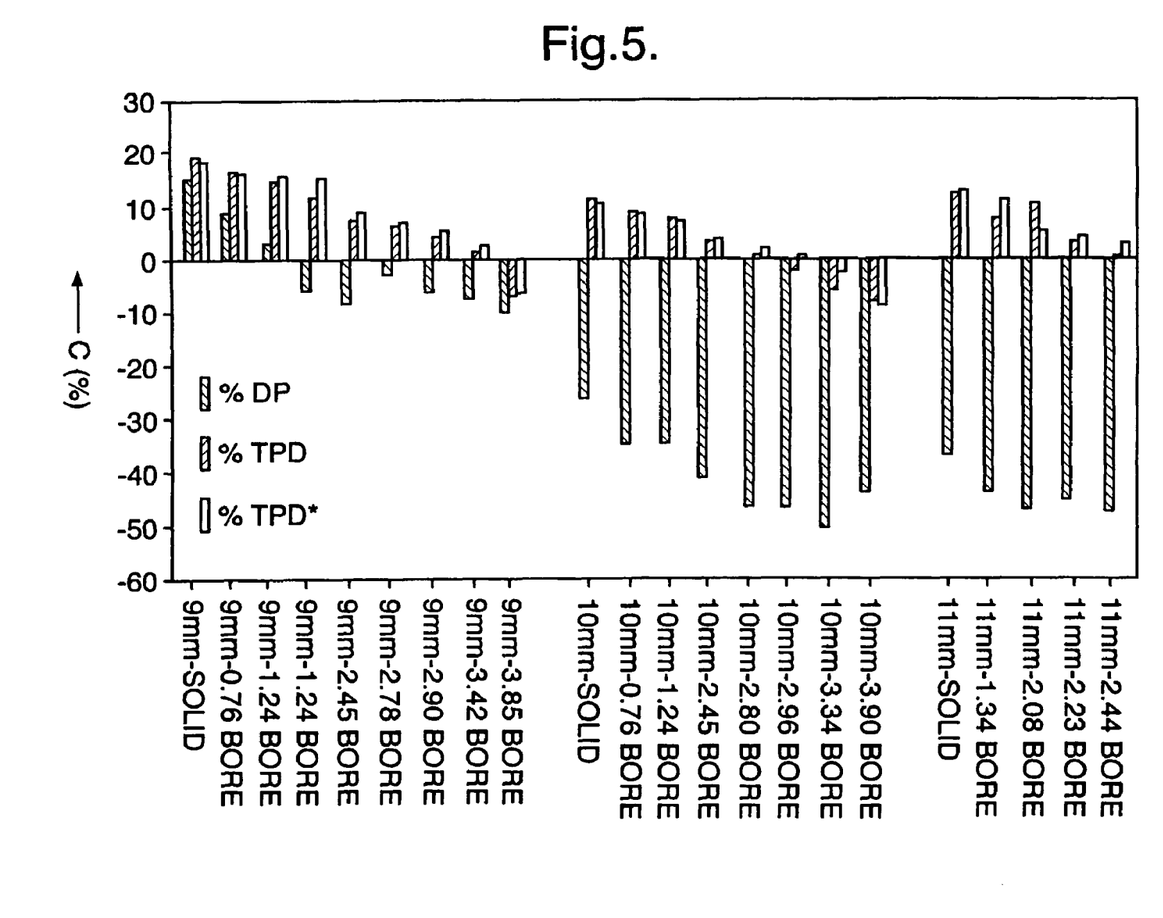
FIG. 5 presents data on the changes ("C (%)") in pressure drop ("% DP") and tube packing density ("% TPD"; "% TPD*" represents duplicate data) resulting from the use of various sizes (outer diameters) of hollow cylinder support material having a nominal length-to-diameter ratio of 1.0 and different bore diameters ("BORE", specified in mm) in a 39 mm diameter reactor tube relative to the use of a standard 8 mm hollow cylinder support.

The data presented in FIG. 5 show an unexpected reduction in pressure drop that results from using the unique combination of reactor tube and support geometry. For the 9 mm carrier having a ratio of bore diameter to outside diameter greater than 0.138 (ratio of outside diameter to bore diameter less than 7.2) there is an improvement in pressure drop, relative to the standard 8 mm carrier tested, and for all the tested 10 mm and 11 mm carrier geometries there is an improvement in pressure drop, relative to the standard 8 mm carrier.

As for the tube packing densities, an improvement is seen in the 9 mm carrier tube packing densities, relative to the standard 8 mm carrier, for geometries in which the ratio of bore diameter to outside diameter is equal or less than about 0.38 (ratio of outside diameter to bore diameter at least 2.6) and, for the 10 mm carrier, an improvement is seen for the geometries having a ratio of bore diameter to outside diameter of equal or less than about 0.28 (ratio of outside diameter to bore diameter greater than 3.4, preferably at least 3.6). For the 11 mm carrier, improvements are seen in both the pressure drop and tube packing density for all the geometries tested, that is at a ratio of outside diameter to bore diameter of greater than 4.5.

EXAMPLE IV

This Example IV presents the results from using the testing procedure described in Example I for nominal carrier sizes 5 mm, 6 mm, 7 mm, 8 mm and 9 mm having a nominal L/D ratio of either 0.5 or 1.0 packed into a 21 mm reactor tube. The particulars of the carrier dimensions have been specified in Example II.

Figure 6:
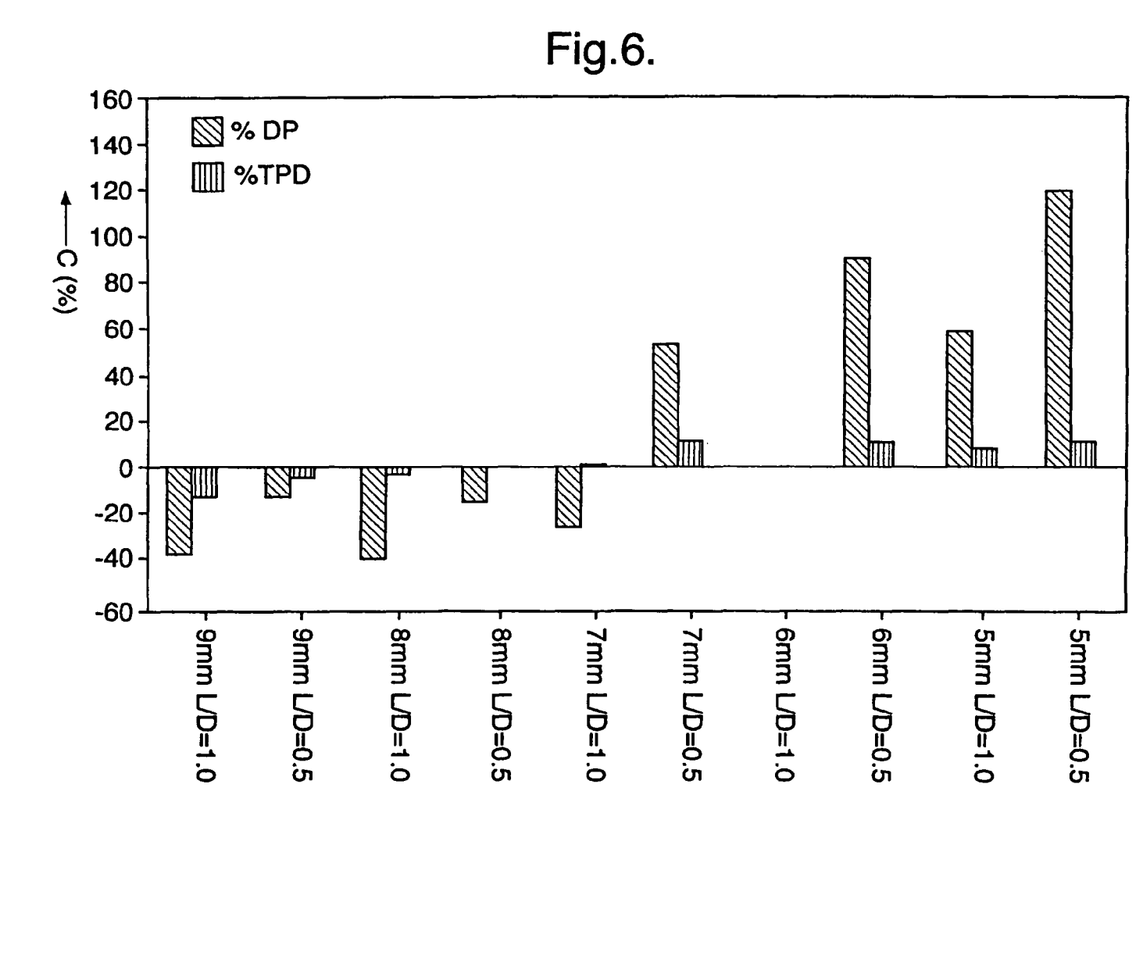
FIG. 6 presents data on the changes ("C (%)")in pressure drop ("% DP") and tube packing density ("% TPD") resulting from the use of various sizes (outer diameters) of hollow cylinder support material with different length-to-diameter ratios ("L/D") in a 21 mm diameter reactor tube relative to the use of a standard 6 mm hollow cylinder support material.

Summary data for the percent changes in pressure drop across the carrier bed and the percent changes in tube packing density relative to the standard 6 mm carrier are presented in FIG. 6. As is shown, for the 8 mm and 9 mm carrier sizes an improvement in pressure drop is observed and for the 7 mm carrier having an L/D of 1.0 an improvement in pressure drop is observed. With selected carriers, an improvement in pressure drop can be achieved, without decreasing the tube packing density, in particular when increasing the ratio of outside diameter to bore diameter.

EXAMPLE V

Hypothetical

Each of the carriers described in Examples II-IV is impregnated with a solution comprising silver, to form a silver catalyst comprising the carrier. A feed stream comprising ethylene and oxygen is then contacted with the catalyst at suitable conditions to form ethylene oxide.

EXAMPLE VI

This Example VI presents information concerning the properties and geometric configuration of the two types of carriers (i.e., Carrier C, and Carrier D) used in the preparation of the catalysts as described in Example VII, (cf. Table 3).

TABLE 3

Properties of Carriers

|  | Carrier C | Carrier D |
|---|---|---|
| Properties | | |
| Water Absorption, % | 46.5 | 50.4 |
| Bulk Packing Density, kg/m³ (lbs/ft³) | 843 (52.7) | 788 (49.2) |
| ASTM Attrition Loss, % | 14.7 | 16.5 |
| Average Flat Plate Crush Strength, N (lbf) | 130 (29.3) | 180 (40.4) |
| Surface Area, m²/g | 0.77 | 0.78 |
| Geometric Configuration | | |
| Nominal Size, mm | 8 | 8 |
| Average Length, mm | 7.7 | 7.7 |
| Length, Range, mm | 6.6-8.6 | 6.6-8.6 |
| Diameter, mm | 8.6 | 8.6 |
| Bore Diameter, mm | 1.02 | 1.02 |
| Ratio Length/Outside Diameter | 0.90 | 0.90 |

EXAMPLE VII

This Example VII describes the preparation of catalysts which can be employed in the present invention.
Catalyst C:
Catalyst C prepared by impregnation of Carrier C using the methods known from U.S. Pat. No. 4,766,105, which U.S. patent is incorporated herein by reference. The final Catalyst C composition was 17.8% Ag, 460 ppm Cs/g catalyst, 1.5 µmole Re/g catalyst, 0.75 µmole W/g catalyst, and 15 µmole Li/g catalyst.
Catalyst D:
Catalyst D was prepared in two impregnation steps. In the first impregnation the carrier was impregnated with a silver solution, according to the procedure for catalyst C, except that no dopants were added to the silver solution. After drying, the resulting dried catalyst precursor contained approximately 17 wt % silver. The dried catalyst precursor was then impregnated with a solution which contained silver and the dopants. The final Catalyst D composition was 27.3% Ag, 550 ppm Cs/g catalyst, 2.4 μmole Re/g catalyst, 0.60 μmole W/g catalyst, and 12 μmole Li/g catalyst.

Catalyst E:

Catalyst E was prepared in two impregnation steps, according to the procedure applied for Catalyst D, except that the tungsten compound was present in the first impregnation solution instead of the second impregnation solution. The final Catalyst E composition was 27.3% Ag, 560 ppm Cs/g catalyst, 2.4 μmole Re/g catalyst, 0.60 μmole W/g catalyst, and 12 μmole Li/g catalyst.

While this invention has been described in terms of the presently preferred embodiment, reasonable variations and modifications are possible by those skilled in the art. Such variations and modifications are within the scope of the described invention and the appended claim.

That which is claimed is:

1. A reactor system for the oxidation of ethylene to ethylene oxide comprising:

an elongated tube having a reaction zoned defined by a tube length and a tube diameter, the tube diameter being at least 28 mm; wherein contained within the reaction zone is a packed bed of shaped support material; and wherein the shaped support material has a hollow cylinder geometric configuration defined by a length an outside diameter and an inside diameter such that the ratio of the length to the outside diameter is in the range of from about 0.5 to about 2, and further such the ratio of the outside diameter to the inside diameter exceeds about 2.7, and the ratio of the tube diameter to the outside diameter is in the range of from about 2 to about 10; wherein the outside diameter is in the range of from about 7.4 mm to about 11.6 mm.

2. The reactor system as recited in claim 1, wherein the tube diameter is in the range of from 28 mm to about 60 mm, and the ratio of the outside diameter to the inside diameter is in the range of from about 3 to about 23.

3. The reactor system as recited in claim 1, wherein the tube diameter is in the range of from 28 mm to about 60 mm, and the ratio of the outside diameter to the inside diameter is in the range of from about 3.3 to about 10.

4. The reactor system as recited in claim 1, wherein the tube diameter is about 39 mm.

5. The reactor system as recited in claim 1, wherein the tube length is in the range of from about 3 to about 15 meters.

6. The reactor system as recited in claim 1, wherein at least 50 percent of the packed bed comprises the shaped support material.

7. The reactor system as recited in claim 1, wherein the ratio of the tube diameter to the outside diameter is in the range of from about 2.5 to about 7.5.

8. The reactor system as recited in claim 7, wherein the ratio of the tube diameter to the outside diameter is in the range of from about 3 to about 5.

9. The reactor system as recited in claim 1, wherein the shaped support material comprises predominantly alpha-alumina, and the packed bed has a tube packing density greater than about 550 kg per cubic meter.

10. The reactor system as recited in claim 1, wherein the shaped support material supports a catalytic component.

11. The reactor system as recited in claim 10, wherein the catalytic component comprises silver.

12. A reactor system for the oxidation of ethylene to ethylene oxide comprising:

an elongated tube having a reaction zone defined by a tube length and a tube diameter, the tube diameter being at least 28 mm; wherein contained within the reaction zone is a packed bed of shaped support material; and wherein the shaped support material has a hollow cylinder geometric configuration defined by a length, an outside diameter and an inside diameter such that the ratio of the length to the outside diameter is in the range of from about 0.5 to about 2, and the ratio of the outside diameter to the inside diameter provides a positive test result, and further such that the ratio of the tube diameter to the outside diameter is in the range of from about 2 to about 10;

wherein the ratio of the outside diameter to the inside diameter exceeds about 2.7;

wherein the outside diameter is in the range of from about 7.4 mm to about 11.6 mm ; and wherein the "positive test result" is defined by a decrease of the quotient of a numerical value of the pressure drop per unit length of the packed bed and a numerical value of the packing density, which numerical values are obtained by testing the packed bed in a turbulent flow of nitrogen gas at a pressure of 1.136 MPa (150 psig), relative to a comparison quotient of numerical values obtained in an identical manner, except that the hollow cylinder geometric configuration of the same support material is defined by a nominal outside diameter of 8 mm and a nominal inside diameter of 3.2 mm, and a ratio of the nominal length to the nominal outside diameter of 1.

13. The reactor system as recited in claim 12, wherein the tube diameter is in the range of from 28 mm to about 60 mm, and the ratio of the outside diameter to the inside diameter is in the range of from about 3 to about 23.

14. The reactor system as recited in claim 12, wherein the tube diameter is in the range of from 28 mm to about 60 mm, and the ratio of the outside diameter to the inside diameter is in the range of from about 3.3 to about 10.

15. The reactor system as recited in claim 12, wherein the tube diameter is about 39 mm.

16. The reactor system as recited in claim 12, wherein the tube length is in the range of from about 3 to about 15 meters.

17. The reactor system as recited in claim 12, wherein at least 50 percent of the packed bed comprises the shaped support material.

18. The reactor system as recited in claim 12, wherein the ratio of the tube diameter to the outside diameter in the range of from about 2.5 to about 7.5.

19. The reactor system as recited in claim 18, wherein the ratio of the tube diameter to the outside diameter in the range of from about 3 to about 5.

20. The reactor system as recited in claim 12, wherein the shaped support material comprises predominantly alpha-alumina, and the packed bed has a tube packing density greater than about 550 kg per cubic meter.

21. The reactor system as recited in claim 12, wherein the shaped support material supports a catalytic component.

22. The reactor system as recited in claim 21, wherein the catalytic component comprises silver.

23. The reactor system as recited in claim 1, wherein the outside diameter is in the range of from about 7.4 to about 8.6 mm and the ratio of the outside diameter to the inside diameter is in the range of from about 3 to about 15.

24. The reactor system as recited in claim 1, wherein the outside diameter is in the range of from about 8.4 to about 9.6 mm and the ratio of the outside diameter to the inside diameter is in the range of from about 3 to about 15.

25. The reactor system as recited in claim 1, wherein the outside diameter is in the range of from about 9.4 to about 10.6 mm and the ratio of the outside diameter to the inside diameter is in the range of from about 4 to about 10.

26. The reactor system as recited in claim 1, wherein the outside diameter is in the range of from about 10.4 to about 11.6 mm and the ratio of the outside diameter to the inside diameter is in the range of from about 4.6 to about 10.

27. The reactor system as recited in claim 12, wherein the outside diameter is in the range of from about 7.4 to about 8.6 mm and the ratio of the outside diameter to the inside diameter is in the range of from about 3 to about 15.

28. The reactor system as recited in claim 12, wherein the outside diameter is in the range of from about 8.4 to about 9.6 mm and the ratio of the outside diameter to the inside diameter is in the range of from about 3 to about 15.

29. The reactor system as recited in claim 12, wherein the outside diameter is in the range of from about 9.4 to about 10.6 mm and the ratio of the outside diameter to the inside diameter is in the range of from about 4 to about 10.

* * * * *